United States Patent [19]

Falotico et al.

[11] Patent Number: 4,822,800
[45] Date of Patent: Apr. 18, 1989

[54] ISOQUINOLINOL COMPOUNDS HAVING CARDIOTONIC AND PHOSPHODIESTERASE FRACTION III INHIBITING PROPERTIES AND/OR RENAL VASODILATING PROPERTIES

[75] Inventors: Robert Falotico, Belle Mead; Ramesh M. Kanojia, Somerville; Jeffery B. Press, Rocky Hill, all of N.J.; Alfonso J. Tobia, Doylestown, Pa.

[73] Assignee: Ortho Pharmaceutical Corporation, Raritan, N.J.

[21] Appl. No.: 871,967

[22] Filed: Jun. 9, 1986

[51] Int. Cl.⁴ ..................... A61K 31/47; C07D 217/24
[52] U.S. Cl. ........................................ 514/309; 546/13; 546/90; 546/141; 546/142
[58] Field of Search .......................... 546/90, 141, 142; 514/309

[56] References Cited

U.S. PATENT DOCUMENTS

| | | | |
|---|---|---|---|
| 2,538,341 | 1/1951 | Ullyot | 546/142 |
| 2,640,829 | 6/1953 | Wilson, III et al. | 546/141 |
| 3,627,469 | 12/1971 | Cheng | 546/142 |
| 3,716,542 | 2/1973 | Lenaers et al. | 546/142 |
| 4,409,017 | 10/1983 | Serban et al. | 546/142 |

OTHER PUBLICATIONS

Blomquist, et al., "Chemical Abstracts", vol. 56, 1962, col. 7225b.

Bell, et al., "Chemical Abstracts", vol. 62, 1965, col. 1632d.
Bellas, et al., "Chemical Abstracts," vol. 62, 1965, col. 1632d.
Popov, et al., "Chemical Abstracts," vol. 82, 1975, col. 140009c.
McKillop, et al., "Chemical Abstracts.," vol. 88, 1978, col. 88:50620q.

Primary Examiner—Richard L. Raymond
Assistant Examiner—James H. Turnipseed
Attorney, Agent, or Firm—Benjamin F. Lambert

[57] ABSTRACT

Substituted 3-isoquinolinol compounds of the general formula

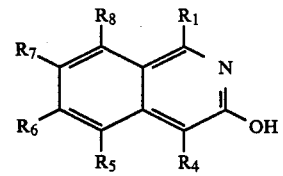

that exhibit cardiotonic, renal vasodilating and phosphodiesterase fraction III properties are pharmacologically active in the treatment of cardiac conditions. Methods for synthesizing and using those compounds are described.

7 Claims, No Drawings

ISOQUINOLINOL COMPOUNDS HAVING CARDIOTONIC AND PHOSPHODIESTERASE FRACTION III INHIBITING PROPERTIES AND/OR RENAL VASODILATING PROPERTIES

DESCRIPTION

1. Technical Field

The present invention relates to 3-isoquinolinol compounds that exhibit cardiotonic, renal vasodilating and phosphodiesterase fraction III inhibiting properties along with methods for synthesizing and using those compounds.

2. Background

Compounds that exhibit cariotonic properties cause cardiac muscle (in particular, the myocardium) to pump more forcefully and effectively. Cardiotonic agents are often used to treat heart failure because they can relieve one of the early effects of the condition—the buildup of fluid in the body tissues. Blood circulation is also improved.

The administration of a cardiotonic agent provides what is known as a "positive inotropic effect" or an increase in the contractile force of cardiac muscle in a dose-dependent manner. Digitalis is one of the most frequently used cardiotonic agents; other examples include ouabain and strophanthidin.

The administration of vasodilators or vasodilating agents produces a relaxation of the muscles of the blood vessels. This has the effect of enlarging the blood vessel passage, reducing resistance to the flow of blood and lowering the blood pressure. As a result, more blood reaches the tissues. Examples of such agents include nitroglycerin, other nitrates, hydralazine and the like. Renal vasodilators, of course, produce a relaxation of the muscles of blood vessels that are associated with the kidneys which results in a corresponding increase in renal blood flow.

Phosphodiesterases convert cyclic-AMP (cyclic adenosine monophosphate or "cAMP") to inactive 5'-AMP. Phosphodiesterase fraction III is one example of a biologically active phosphodiesterase. Compounds including theophylline and caffeine inhibit phosphodiesterase activity and its breakdown of cAMP; therefore, a high level of cAMP in the blood is maintained.

Compounds that exhibit cardiotonic and vasodilating properties and which also inhibit the hydrolytic activity of phosphodiesterases would be a substantial improvement over currently available compounds that do not possess each of the foregoing properties.

A number of compounds that are structurally related to isoquinolines and isoquinolinols have been described in the literature.

U.S. Pat. Nos. 3,798,225, 3,910,927 and 4,015,006 to Kreighbaum et al. (Mead Johnson & Co.) relate to 2-substituted-3(2H)-isoquinolones and 2-substituted-3-alkoxyisoquinolines that are reported to have hypotensive and peripheral vasodilating properties upon oral administration. The patents relate in particular to 1-benzyl derivatives of the above compounds.

The preparation of 3-hydroxy-6,7-dimethoxy-1-methylisoquinoline and the corresponding tautomeric form, 6,7-dimethoxy-1-methyl-3(2H)-isoquinoline, which is the parent compound of several compounds of this invention, has been reported along with the preparation of the corresponding 3-ethyl ether and 3-acetate derivatives. [Bentley et al., *J. Chem Soc.*, 1763 (1952); Dorofeenko et al., *USSR Author's Certificate No.* 207,921, CA, 69, 52003x (1967) and D. A. Evans et al., *J. Chem Soc. (B);* 590 (1967).].

1-Phenylisoquinoline derivatives are described in Ger. Offen. DE. No. 3,227,741 which issued to Hoechst AG. The compounds are reported to exhibit antidepressant activity. U.S. Pat. Nos. 4,282,222 and 4,282,223 to Bartmann et al. (assigned to Hoechst AG) describe isoquinolines including 3-piperidino, 3-piperazino and 3-piperazino N-substituted derivatives that are reported to exhibit antidepressant activity.

U.S. Pat. No. 3,641,032 to Zinnes et al. (Warner-Lambert Company) describes immunosuppressive compositions that include 2-ethyl-3-hydroxy-1(2H)-isoquinolone diphenylcarbamate.

U.S. Pat. No. 3,954,771 to Geerts et al., which patent is assigned to UCB Society Anonyme, describes a process for the preparation of 2H-3-isoquinolones. The foregoing compounds are described as precursors for the synthesis of 1,4-dihydro-1,4-ethanoisoquinoline-3(2H)ones (described in U.S. Pat. 3,781,436) that are reported to be active in the central nervous system (CNS-active) for the treatment of disorders including insomnia and vertigo.

U.S. Pat. No. 4,041,077 to Chosez et al. (UCB Societe Anonyme) describes the use of N-benzyl-2,2-dimethoxyacetamides in the synthesis of 2H-3-isoquinolones which, in turn, may be used in the synthesis of 1,4-dihydro-1,4-ethenoisoquinolin-3(2H)ones.

DETAILED DESCRIPTION OF THE INVENTION

3-Isoquinolinols, pharmaceutical compositions containing a 3-isoquinolinol compound as an active ingredient, methods of treating a mammal exhibiting a cardiac condition and methods for synthesizing the present compounds are contemplated. The terms "3-isoquinolinol", "isoquinolinol" and grammatical forms thereof are used herein to indicate the useful compounds of the present invention.

In particular, the invention contemplates a 3-isoquinolinol having a structure that corresponds to the formula I:

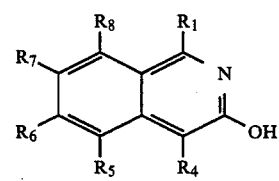

wherein $R_1$ is a radical selected from the group consisting of hydrogen, lower alkyl, aryl and halogen substituted radicals thereof;

$R_4$ is a radical selected from the group consisting of hydrogen, halogen, lower alkyl, cycloalkyl containing 5-7 carbon atoms and $-(CH_2)_n-Y$ wherein Y is hydroxy, OR, OCOR, $CF_3$, COR, COOR, $CON(R)_2$, cyano and halogen, wherein R can be hydrogen, lower alkyl and cycloalkyl containing 5-7 carbon atoms, and n is an interger from 0 to about 10, inclusive, preferably from 1 to about 4; and $R_5$, $R_6$, $R_7$ and $R_8$ may be independently selected from the group consisting of hydrogen, halogen, hydroxy, and lower alkoxy, $R_5$ and $R_6$, $R_6$ and $R_7$ and $R_7$ and $R_8$ when taken together can form $O-CH_2-O$ (methylenedioxy).

3-Isoquinolinol compounds that contain a substituent $R_4$ (as defined herein), in any combination with substituents $R_1$, $R_5$–$R_8$ (as further defined herein and present either singly or in combination) have not been previously reported. In addition, several of the parent 3-isoquinolinols wherein $R_4$ is hydrogen are also novel chemical entities. The compounds having structures that correspond to the foregoing formula are also capable of existing as the corresponding 3-keto tautomeric forms.

Also contemplated are pharmaceutically acceptable salts of the compounds of this invention. Any conventional pharmaceutically acceptable salt can be used. Among the salts that can be prepared are alkali metal salts including lithium, sodium and potassium; alkaline earth metal salts including calcium and magnesium; and aluminum, zinc and iron. Such salts can be formed from the compounds of the present invention which include a carboxylic acid group by treating the acid in a conventional manner with a base such as a metal hydroxide or ammonium hydroxide.

Since the compounds of the present invention can include more than one carboxylic acid group, partial salts or partial lower alkyl esters (compounds in which not all the carboxylic acid-functional groups are in salt or ester form) are contemplated, as are mixed salt/ester forms.

Also contemplated are the hydrohalide, in particular the hydrobromide and hydrochloride salts, as well as other pharmaceutically acceptable salts, such as sulfates, phosphates and the like of the isoquinolinols of this invention.

Exemplary compounds of the present invention whose structures conform to the above formula are listed in Table 1, below.

TABLE 1

3-Isoquinolinol Derivatives

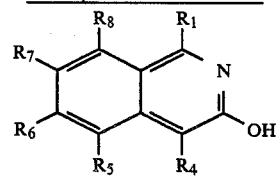

| Compound | Prepared According to Example | $R_1$ | $R_4$ | $R_5$ | $R_6$ | $R_7$ | $R_8$ | Melting Point °C. |
|---|---|---|---|---|---|---|---|---|
| A | 3a | $CH_3$ | H | H | OH | OH | H | >300(d) |
| B | 1a | $CH_3$ | $CH_2CH_2CO_2CH_3$ | H | $OCH_3$ | $OCH_3$ | H | 198–200 |
| C | 2 or 1b | $CH_3$ | H | H | H | $OCH_3$ | $OCH_3$ | 165–166 |
| D | 1b | H | H | H | H | $OCH_3$ | $OCH_3$ | 130–132 |
| E | 4 | $CH_3$ | $CH_2CH_2CO_2H$ | H | $OCH_3$ | $OCH_3$ | H | 251–253 |
| F | 4 | $CH_3$ | $CH_2CH_2CO_2H$ | H | $OCH_3$ | $OCH_3$ | H | 117–119 |
| G | 3a | $CH_3$ | $CH_2CH_2CO_2H$ | H | OH | OH | H | >300(d) |
| H | 1a | $CH_3$ | H | H | $OCH_3$ | $OCH_3$ | $OCH_3$ | 232–233 |
| I | 3a | $CH_3$ | H | H | H | OH | OH | 247–249(d) |
| J | 1a | $CH_3$ | $CH_2CH_2CO_2CH_3$ | H | $OCH_3$ | $OCH_3$ | $OCH_3$ | 170–171 |
| K | 1a | $C_2H_5$ | $CH_2CH_2CO_2CH_3$ | H | $OCH_3$ | $OCH_3$ | H | 181–183 |
| L | 1a | $CH_3$ | $CH_2CH_2CO_2CH_3$ | H | O—$CH_2$—O | | H | 213–216 |
| M | 1a | n-$C_3H_7$ | $CH_2CH_2CO_2CH_3$ | H | $OCH_3$ | $OCH_3$ | H | 194–196 |
| N | 3b | $CH_3$ | $CH_2CH_2CO_2H$ | H | OH | OH | $OCH_3$ | 172–174 |
| O | 1a | $CH_3$ | $CH_2CH(CH_3)CO_2CH_3$ | H | $OCH_3$ | $OCH_3$ | H | 186–187 |
| P | 1a | i-$C_3H_7$ | $CH_2CH_2CO_2CH_3$ | H | $OCH_3$ | $OCH_3$ | H | 159–160 |
| Q | 1b | H | $CH_2CH_2CO_2CH_3$ | H | $OCH_3$ | $OCH_3$ | H | 178–180 |
| R | 5 | $CH_3$ | $CH_2CH_2CO_2CH(CH_3)_2$ | H | $OCH_3$ | $OCH_3$ | H | 188–189 |
| S | 5 | $CH_3$ | $CH_2CH_2CO_2C_2H_5$ | H | $OCH_3$ | $OCH_3$ | H | 178–180 |
| T | 5 | $CH_3$ | $CH_2CH_2CO_2\underline{c}C_5H_9$ | H | $OCH_3$ | $OCH_3$ | H | 200–202 |
| U | 1b | H | $CH_2CH_2CO_2CH_3$ | H | O—$CH_2$—O | | H | 208–212 |
| V | 6 | $CH_3$ | $CH_2CH_2CONH_2$ | H | $OCH_3$ | $OCH_3$ | H | 259–261 |
| W | 1a | $CH_3$ | $CH_2CO_2CH_3$ | H | $OCH_3$ | $OCH_3$ | H | 243–245 |
| X | 6 | $CH_3$ | $CH_2CH_2CONHCH_3$ | H | $OCH_3$ | $OCH_3$ | H | 265–267 |
| Y | 1a | $CH_3$ | $CH_2CH_2CH_3$ | H | $OCH_3$ | $OCH_3$ | H | 253–255 |
| Z | 1a | $CH_3$ | $CH_2CH_3$ | H | $OCH_3$ | $OCH_3$ | H | 272–274 |
| AA | 6 | $CH_3$ | $CH_2CH_2CON(CH_3)_2$ | H | $OCH_3$ | $OCH_3$ | H | 214–216 |
| AB | 1a | $CH_3$ | $CH_3$ | H | $OCH_3$ | $OCH_3$ | H | 295–297(d) |
| AC | 7a | $CH_3$ | Br | H | $OCH_3$ | $OCH_3$ | H | 175–178 |
| AD | 7b | $CH_2Cl$ | Cl | H | $OCH_3$ | $OCH_3$ | H | >310 |
| AE | 7b | $CH_3$ | Cl | H | $OCH_3$ | $OCH_3$ | H | >300(d) |
| AF | 1a | $CH_3$ | $CH(CH_3)_2$ | H | $OCH_3$ | $OCH_3$ | H | 223–225 |
| AG | 7b | $CH_3$ | Cl | H | O—$CH_2$—O | | H | >300(d) |
| AH | 1a | $CH_3$ | H | H | $OCH_3$ | H | $OCH_3$ | 280–282(d) |
| AI | 1a | $CH_3$ | H | H | $OCH_3$ | H | H | 255–258(d) |
| AJ | 1a | $CH_3$ | $CH_2CH(CH_3)_2$ | H | $OCH_3$ | $OCH_3$ | H | 213–214 |
| AK | 1a | $CH_3$ | H | H | $OCH_3$ | $OC_2H_5$ | H | 235–240(d) |
| AL | 1a | $CH_3$ | H | H | $OCH_3$ | $OC_4H_9\underline{n}$ | H | 213–214(d) |
| AM | 1a | $CH_3$ | H | $OCH_3$ | $OCH_3$ | H | H | 216–218(d) |
| AN | 1a | $CH_3$ | $\underline{c}$-$C_5H_9$ | H | $OCH_3$ | $OCH_3$ | H | 282–284(d) |
| AO | 1a | $CH_3$ | H | H | $OC_2H_5$ | $OC_2H_5$ | H | 231–232(d) |
| AP | 1a | $CH_3$ | $CO_2CH_3$ | H | $OCH_3$ | $OCH_3$ | H | 249–251(d) |
| AQ | 1b | H | H | H | $OCH_3$ | $OC_2H_5$ | H | 248–250 |
| AR | 1b | $CH_3$ | H | H | H | $OCH_3$ | H | 227–230 |
| AS | 1a | $CH_3$ | $C_2H_5$ | H | $OCH_3$ | $OC_2H_5$ | H | 250–252 |
| AT | 6 | $CH_3$ | CONHCH$_3$ | H | $OCH_3$ | $OCH_3$ | H | 316–318(d) |
| AU | 1b | $CH_3$ | H | Br | H | $OCH_3$ | $OCH_3$ | 237–240 |
| AV | 6 | $CH_3$ | $CONHNH_2$ | H | $OCH_3$ | $OCH_3$ | H | >300(d) |

TABLE 1-continued

3-Isoquinolinol Derivatives

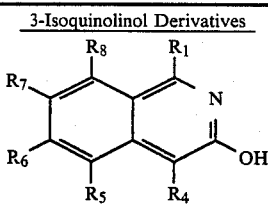

| Compound | Prepared According to Example | $R_1$ | $R_4$ | $R_5$ | $R_6$ | $R_7$ | $R_8$ | Melting Point °C. |
|---|---|---|---|---|---|---|---|---|
| AW | 1a | $CH_3$ | H | H | $OC_2H_5$ | $OCH_3$ | H | 270–275 |

(d) = with decomposition.
c = cyclo.
i = iso.
n = normal.

As used herein, the term "lower alkyl", in its various uses, indicates a branched or straight chain hydrocarbon having 1 to about 8 carbon atoms, and particularly 1 to about 4 carbon atoms. Lower alkyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1-octyl, 2-octyl and the like.

The term "aryl", as used herein alone or in combination with other terms, indicates aromatic hydrocarbon groups which can be unsubstituted or substituted with one or more lower alkyl radicals or halogens selected from chloro, bromo, iodo and fluoro functionalities. A preferred aryl group is phenyl.

The phrase "halogen-substituted radical" indicates a lower alkyl or aryl group (in the case of $R_1$) and a lower alkyl or cycloalkyl group (in the case of $R_4$ and R) that includes a halogen selected from chloro, bromo, iodo and fluoro functionalities, with chloro and bromo functionalities being preferred.

The term "cycloalkyl" indicates a cyclic hydrocarbon having from 3 to 8 carbon atoms, and preferably 5 or 6 carbon atoms.

The term "lower alkoxy" indicates a lower alkyl group (as defined above) that includes a terminal oxygen bonded to one or more carbon atoms of the isoquinoline ring (at positions $C_5$–$C_8$, inclusive). Examples include methoxy, ethoxy, propoxy, isopropoxy, n-butoxy, 2-methylpentoxy and the like, with lower alkoxy having 1 to about 4 carbon atoms being particularly preferred.

In particularly preferred practice, $R_1$ is lower alkyl or halogen-substituted lower alkyl, most preferably $C_1$–$C_4$ lower alkyl and halogen-substituted $C_1$–$C_9$ lower alkyl, $R_4$ is hydrogen, lower alkyl, halogen or $(CH_2)_n$—Y where Y is COOR where R is lower alkyl and n is an integer from 1 to about 4, $R_5$ is hydrogen, $R_6$ and $R_7$ are both lower alkoxy, and most preferably $C_1$–$C_4$ lower alkoxy, or together are methylenedioxy, and $R_8$ is hydrogen or methoxy.

In an additional preferred embodiment, $R_1$ is methyl, $R_4$ is lower alkyl, $R_5$ is hydrogen, $R_6$ and $R_7$ are methoxy or ethoxy and $R_8$ is hydrogen.

A pharmaceutical composition that comprises an effective amount of an above-described 3-isoquinolinol dispersed in a pharmaceutically acceptable carrier is also contemplated herein. The composition comprises a unit dosage of the isoquinolinol.

The isoquinolinols of this invention have cardiotonic and renal vasodilating properties and are capable of inhibiting the hydrolytic activity of phosphodiesterase fraction III. In preferred practice, the isoquinolinol of the pharmaceutical composition is capable of producing the desired cardio-stimulating and vasodilating effects and inhibiting the hydrolytic activity of phosphodiesterase fraction III in the amount at which that isoquinolinol is present in the pharmaceutical composition.

The term "unit dosage" and its grammatical equivalents are used herein to refer to physically descrete units suitable for administration to human patients and to warm-blooded mammals. Each unit contains a predetermined effective amount of the active ingredient calculated to produce the desired cardio-stimulating, vasodilating and phosphodiesterase inhibiting effect in association with the required physiologically tolerable carrier, e.g., a diluent or a vehicle.

The specification for the novel unit dosage forms of this invention are dictated by and are directly dependent on (a) the unique characteristics of the active ingredient, and (b) the limitations inherent in the art of compounding such an active ingredient for therapeutic use in humans and other mammals. Examples of suitable unit dosage forms in accord with this invention are tablets, capsules, pills, powder packets, granules, wafers, and the like, segregated multiples of any of the foregoing, along with liquid solutions, liquid suspensions, elixirs and aerosol suspensions.

The active ingredient is referred to herein as being dispersed in the carrier. Thus, the dispersion formed can be a simple admixture, a non-settling dispersion as in the case of certain emulsions or as an ultimate dispersion, a true solution. In such compositions, the active ingredient is ordinarily present in an amount of at least about 0.5 percent by weight based on the total weight of the composition to about 90 percent by weight.

The effective amount of active ingredient that is administered in vivo depends on the age and weight of the mammal treated, the particular condition to be treated, the frequency of administration, and the route of administration. Exemplary unit doses can contain about 0.05 to about 50 milligrams per kilogram of body weight, more preferably about 0.1 to about 10 milligrams per kilogram of body weight per day. The human adult dose is typically in the range of about 100 to about 500 milligrams daily, given as a single dose or in 3 or 4 divided doses. Veterinary dosages correspond to human dosage with the amounts administered being in proportion to the weight of the animal as compared to adult humans.

However, it will be understood that the amount administered is determined by the physician or veterinarian in light of the relevant circumstances including the condition to be treated, the compound to be administered and the route of administration. Therefore, the foregoing dosage ranges are not intended to limit the scope of this invention in any way.

Liquid compositions can also contain liquid phases in addition to or to the exclusion of water. Exemplary of such additional liquid phases are glycerin and vegetable oils including peanut oil and cottonseed oil.

Suitable solid carriers (diluents) include those materials usually used in the manufacture of pills or tablets, and include corn starch, lactose, dicalcium phosphate, thickeners such as tragacanth and methylcellulose U.S.P., finely divided silica, polyvinylpyrrolidone, magnesium stearate and the like. Antioxidants such as methylparaben and propylparaben can be present in both solid and liquid compositions, as can sweeteners such as cane sugar, beet sugar, sodium saccharin, sodium cyclamate and the dipeptide methyl ester sweetener sold under the trademark NUTRASWEET (aspartame) by G. D. Searle Co., Skokie, IL.

Methods for stimulating cardiac contractions and for increasing the contractile force of cardiac muscle in a mammal are also contemplated. The methods comprise administering to that mammal a unit dose of a pharmaceutical composition that includes an effective amount of an active ingredient that is an aforementioned 3-isoquinolinol dispersed in a pharmaceutically acceptable carrier. The pharmaceutical composition is preferably maintained within the mammal until the isoquinolinol is cleared from the body of the mammal by natural means such as metabolism or excretion.

The pharmaceutical composition can be administered orally, by injection, by inhalation (for example, in the form of an aerosol, micropulverized powder or nebulized solution) as a tablet, capsule or aqueous dispersion or by any other means well known in the art.

Inasmuch as a pharmaceutical composition can be administered 3 or more times daily (during a 24 hour period), the method of stimulating cardiac contractions can include the serial administration of the pharmaceutical composition into the treated mammal over a given time period; for example, weeks, months or years. In preferred practice, the pharmaceutical composition is administered to the mammal a number of times over a period of about thirty days.

Methods for synthesizing 3-isoquinolinol compounds are other aspects of the present invention.

The Examples included herein illustrate the preparation of a number of isoquinolinol compounds according to the present invention. By way of summary, the preferred compounds of this invention may be prepared in the following manner.

METHODS OF PREPARATION

3-Isoquinolinol compounds of this invention can be prepared by one of the following general methods.

Method 1

In formula I when $R_6$ is an electron donating substituent, for example, a lower alkyl, lower alkoxy, halogen or acetamido radical, the compound can be prepared by either formylating (wherein $R_1$ is hydrogen) or acylating (wherein $R_1$ is lower alkyl or aryl) a phenyl compounds of formula II wherein A is CN (phenylacetonitrile) or COOR [phenylacetic acid derivative in which R is hydrogen or lower alkyl] and $R_5$ to $R_8$ are

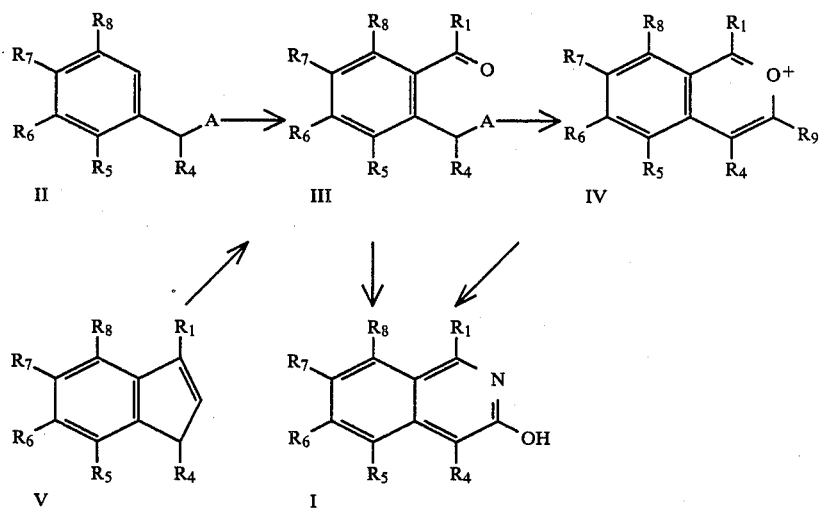

as already defined and $R_4$ is hydrogen, lower alkyl, aryl, acyl, or $(CHR)_n$—B wherein n is an integer from about 0 to about 10, B can be OR, COOR, or a halogen, wherein R is lower alkyl, substituted lower alkyl or aryl.

Formylation of II to give the o-formyl derivative III (wherein $R_1$ is hydrogen) can be performed by electrophilic substitution with HCN or a metal cyanide salt and acid or with a formic acid derivative including, for example, $Cl_2CHOCH_3$, formamide, dimethylformamide and the like and a Lewis acid catalyst such as $ZnCl_2$, $SnCl_4$, $AlCl_3$, $ZrCl_4$, $TiCl_4$, $BF_3$ etherate, and the like. Acylation of II to provide O-acyl derivative III (where $R_1$ is lower alkyl or aryl) can be similarly effected under conventional Friedel-Crafts reaction conditions using either an acid chloride ($R_1COCl$), acid anhydride [$(R_1CO)_2O$] or an acid ($R_1COOH$) and a Lewis acid catalyst, such as including $AlCl_3$, $ZrCl_4$, $TiCl_4$, $FeCl_3$, $ZnCl_2$, $SnCl_4$, $BF_3$ etherate, $HClO_4$, $(CF_3CO)_2O$, $CF_3SO_3H$, or polyphosphoric acid (PPA). The o-acylphenylacetic acid derivative III can also be prepared by other methods such as oxidative ring opening of an appropriately substituted 1-indene derivative (V).

The o-formyl or o-acyl derivative II can either be directly converted to the isoquinoline derivative I upon reaction with ammonium hydroxide, ammonia or an acid salt thereof including ammonium acetate, ammonium carbonate and the like.

Alternatively, the o-formyl or o-acyl derivative III can be first treated with a strong acid including, for example, perchloric acid, trifluoroacetic acid, trifluorosulfonic acid, boron trifluoride etherate and the like to form a 2-benzopyrylium salt IV wherein $R_9=OR$ (when $A=COOR$ in II) or $NHCOR_1$ (when $A=CN$ in II) having R and $R_1$ as described above. Treatment of the 2-benzopyrylium salt IV with ammonia or ammonium hydroxide in a solvent, for example, water, a lower alkanol such as ethanol, n-propanol or t-butanol, an ether such as diethyl ether or ethylene glycol diethyl ether, tetrahydrofuran (THF), a hydrocarbon such as benzene or toluene or a chlorohydrocarbon including methylene chloride, chloroform or carbon tetrachloride at zero degrees C. to about 150 degrees C. provides the isoquinolinol derivative I.

Method 2

3-Isoquinolinol compounds I wherein $R_4$ is halogen and the like preferably are prepared by electrophilic substitution at $C_4$ of I (wherein $R_4$ is hydrogen). Thus, for example, treating I with two equivalents of a halogen such as chlorine or bromine in acetic acid, chloroform, benzene and the like provides the hydrohalide (HX) salt of 4-halogenated derivative which upon neutralization with a base provides the 4-halogenated-3-isoquinolinol free base I (wherein $R_4$ is chloro or bromo). In the alternative, treatment with an appropriate N-halosuccinimide or similar reagent such as sulfuryl chloride or sulfuryl bromide (one equivalent) directly provides the 4-halogenated compound I (wherein $R_4$ is chloro, bromo or iodo).

Method 3

Isoquinolinol compounds of the general formula I containing $R_7$ as an electron releasing group and $R_1$-$R_8$ (as defined above) can be prepared by the Pomeranz-Fritsch type cyclization of an appropriately substituted intermediate (VI) with an acid such as sulfuric acid, PPA, $BF_3$ etherate and the like.

Compound VI can be prepared by reacting a benzylamine with acid derivative VII wherein X is halogen; OR and R are lower alkyl radicals and $R_4$ is as defined above. Alternatively, Compound VI can be prepared by displacing an appropriate benzyl halide by an amide anion derived from amide VIIa.

Method 4

Isquinoline compounds I wherein $R_4$ is CN, COOR, $CONH_2$ or acyl can also be prepared by reacting o-acylhalobenzene VIII, wherein X is chloro, bromo or iodo, with a reactive methylene compound IX where P=CN, $CONH_2$ and $R_4$=CN, COR, COOR in the presence of a base including NaOR, NaH and $NaNH_2$ in solvents including ROH, $RO(CH_2)_2OR$, THF and benzene in the presence of a cuprous halide catalyst at about 60° C. to about 120° C. (wherein R is hydrogen, lower alkyl or aryl).

A list of compounds that correspond to the foregoing formula, their biological activities and experimental procedures for their preparation are included in the following discussion.

A series of 3-isoquinolinols that were synthesized according to the various methods of the present invention are listed in Table 1, hereinbefore.

Intermediates are prepared as described in Examples 8-10. For example, intermediate 2-benzopyrylium salts IV listed in Table 2, were prepared according to Examples 8a-d. Intermediates II, listed in Table 3, were prepared according to Examples 10a-c, intermediates III ($R_1$ is hydrogen and methyl) according to Examples 8e (1), 8e(2), 8f and 8g, and intermediates VI according to Examples 9a(1), 9a(2) and 9b.

Having generally described the invention, a more complete understanding can be obtained by reference to the following Examples, which are included for illustrative purposes only and are not intended to be limiting.

BEST MODES OF CARRYING OUT THE INVENTION

In the following Examples, melting points (mp) were determined on a Thomas-Hoover apparatus, and the melting points reported herein are uncorrected. The infrared (IR) spectra were recorded on a Beckman Instruments IR-8 spectrophotometer and are expressed in microns. Nuclear magnetic resonance (NMR) spectra for hydrogen atoms were obtained in the indicated solvent with tetramethylsilane (TMS) as the internal standard on a Varian T-60A or an IBM WP-100 spectrometer. The values are expressed in δ units (parts per million downfield from TMS). Parenthesized, underlined hydrogens were assigned to the resonance positions immediately before the parentheses. Mass spectra were obtained on a Finnigan 1015D quadrupole mass spectrometer coupled to a Finnigan 9500 gas chromatograph or on a Finnigan MAT 8230 Double Focusing high resolution mass spectrometer.

EXAMPLE 1a 4-(β-Carbomethoxyethyl)-3-hydroxy-6,7-dimethoxy-1-methylisoquinoline (Compound B)

To an ice cooled and mechanically stirred slurry of 2.246 grams 4-β-carbomethoxyethyl-3,6,7-trimethoxy-1-methyl-2-benzopyrylium boron trifluoride salt (5.95 mmol) (which is the product of Example 8a) in 2 ml water were added 60 ml concentrated ammonium hydroxide over a 10 minute period. The mixture was stirred for an additional 20 minutes. The yellow precipitate that formed was filtered, washed with water and dried to provide 1.07 grams of crude Compound B (59% yield). Recrystallization from ethanol provided 0.747 grams of pure Compound B having a melting point of 198°–200° C.

$^1$H NMR (CDCl$_3$): δ 2.65 (triplet, J=7 Hz, 2 H, CH$_2$CH$_2$COOCH$_3$); δ 2.78 (singlet, 3 H, 1—CH$_3$); δ 3.23 (multiplet, 2 H, CH$_2$COOCH$_3$); δ 3.62 (singlet, 3 H, COOCH$_3$); δ 3.92 (singlet, 3 H, OCH$_3$); δ 4.00 (singlet, 3 H, OCH$_3$); δ 6.82 (singlet, 1 H, ArH); δ 6.92 (singlet, 1 H, ArH).

IR (KBr): 5.81, 6.12, 6.39, 6.71μ.

Mass spectrum: m/e 305 (M+).

Anal. Calculated for C$_{16}$H$_{19}$NO$_5$: C, 62.94; H, 6.27; N, 4.59. Found: C, 62.63; H, 6.15; N, 4.62.

Use of the above procedure with the appropriately substituted 2-benzopyrylium salts (formula IV), principally as the perchlorate salts, provided a large number of 3-isoquinolinols (Formula I) as shown in Table 1.

EXAMPLE 1b 4-(β-Carbomethoxyethyl)-3-hydroxy-6,7-dimethoxyisoquinoline (Compound Q)

A mixture of 8.34 grams of dimethyl 2-(2-formyl-4,5-dimethoxyphenyl)glutarate (25.74 mmol) (which is the product of Example 8e(1)), 17.86 grams anhydrous ammonium acetate (232 mmol) and 15 ml glacial acetic acid was heated to 75° C. and was maintained at that temperature for 30 minutes. After cooling, the yellow precipitate was isolated by filtration, washed with water and dried to provide 5.78 grams of Compound Q (77% yield). Recrystallization from methanol and trituration with ether (to remove any trace amounts of methanol) provided 4.57 grams of pure Compound Q having a melting point of 178° to 180° C.

$^1$H NMR (CDCl$_3$): δ 2.68 (triplet, J=7 Hz, 2 H, CH$_2$CH$_2$COOCH$_3$); δ 3.27 (triplet, J=7 Hz, 2 H, CH$_2$COOCH$_3$); δ 3.63 (singlet, 3 H, COOCH$_3$); δ 3.93 (singlet, 3 H, OCH$_3$); δ 4.02 (singlet, 3 H, OCH$_3$); δ 6.83 (singlet, 1 H, ArH); δ 6.97 (singlet, 1 H, ArH); δ 8.20 (singlet, 1 H, 1-H); δ 13.4 (broad singlet, 1 H, 3-OH).

IR (KBr): 5.75, 6.09, 6.33, 6.71μ.

Mass spectrum: m/e 291 (M+).

Anal. Calculated for C$_{15}$H$_{17}$NO$_5$: C, 61.85; H, 5.88; N, 4.81. Found: C, 61.88; H, 5.98; N, 4.63.

EXAMPLE 2

3-Hydroxy-7,8-dimethoxy-1-methylisoquinoline (Compound C)

Polyphosphoric acid was freshly prepared by adding 130 ml phosphoric acid (an 87% aqueous solution) to phosphorous pentoxide. The mixture reacted exothermically and reached a temperature of 100° C. The mixture was rapidly stirred and was maintained at about 100° C. with an oil bath for about 4 hours until all the phosphorous pentoxide dissolved. To this colorless, viscous liquid heated to 93° C. were added 9.62 (30.9 mmol) N-[1-(2,3-dimethoxyphenyl)ethyl]diethoxyacetamide (VI), and the resulting deep red solution was maintained with stirring at 88°–98° C. for 1.5 hours. The reaction mixture was cooled to room temperature and maintained at that temperature overnight. The mixture was then poured into 500 ml ice-water, and the pH were adjusted to 6.8 by adding solid potassium hydroxide. The yellow precipitate that formed was filtered, washed with water and dried to provide 6 grams of the solid. The filtrate was extracted five times with 300 ml chloroform per extraction. The organic layer was dried over sodium sulfate, filtered and evaporated to dryness in vacuo to provide an additional 0.8 grams of the yellow precipitate. The two portions of the yellow precipitate were combined to provide 6.8 grams of material which was chromatographed on a silica gel column (280 grams, 20 mm ID). Elution with a 93:7 methylene chloride:methanol mixture provided 1.4 grams of Compound C (21% yield) which was further purified by recrystallization from ethyl acetate to provide 0.770 grams pure Compound C (11.3% yield) having a melting point of 165° to 166° C.

$^1$H NMR (TFA): δ 3.40 (singlet, 3 H, 1-CH$_3$); δ 4.15 (singlet, 3 H, OCH$_3$); δ 4.20 (singlet, 3 H, OCH$_3$); δ 7.38 (singlet, 1 H, 4-H); δ 7.68 (doublet, J=9 Hz, 1 H, ArH); δ 7.97 (doublet, J=9 Hz, 1 H, ArH).

IR (KBr): 6.06μ.

Mass spectrum: m/e 219 (M+).

Anal. Calculated for C$_{12}$H$_{13}$NO$_3$: C, 65.74; H, 5.98; N, 6.39. Found: C, 65.42; H, 6.09; N, 6.23.

EXAMPLE 3a

4-β-Carboxyethyl-3,6,7-trihydroxy-1-methyl-3-isoquinoline Hydrobromide (Compound G)

A slurry of 1.5 grams 4-β-carbomethoxyethyl-3-hydroxy-6,7-dimethoxy-1-methoxy-isoquinoline (4.92 mmol) (Compound B) in 15 ml acetic acid was treated with 10 ml of 48% hydrobromic acid, and the mixture was refluxed overnight under a nitrogen atmosphere. The crystalline hydrobromide salt was isolated by cooling the reaction mixture, filtering the mixture to separate the precipitate, triturating with acetone and ether, and drying the precipitate in vacuo to provide 1.2 grams of Compound G (71% yield), having a melting point greater than 300° C.

$^1$H NMR (DMSO-d6): δ 2.28–2.68 (multiplet, 2 H, CH$_2$CH$_2$COOH); δ 2.93–3.33 (multiplet, 2 H, CH$_2$COOCH); δ 7.25 (singlet, 1 H, ArH); δ 7.42 (singlet, 1 H, ArH); δ 10.93–11.47 (multiplet, 3 H, ArOH and COOH).

IR (KBr): 2.99–3.64, 5.88, 6.13, 6.60μ.

Mass spectrum: m/e 291 (M+).

Anal. Calculated for C$_{13}$H$_{13}$NO$_5$HBr: C, 45.37; H, 4.10; N, 4.07. Found: C, 45.39; H, 4.15; N, 3.96.

EXAMPLE 3b

4-Carboxyethyl-3,6,7-trihydroxy-8-methoxy-1-methylisoquinoline Hydrobromide 1.5 Hydrate (Compound N)

Boron tribromide (25.0 grams, 99.8 mmol) was added dropwise to a solution of 2.14 grams 4-carbomethoxyethyl-3-hydroxy-6,7,8-trimethoxy-1-methylisoquinoline (6.38 mmol) (Compound J) in 35 ml methylene chloride cooled to −50° C. (in a dry ice-acetone slush bath) under a nitrogen atmosphere. A gummy residue formed immediately. The reaction mixture was warmed to room temperature, stirred for 4 hours and then was cooled to 0°–5° C. Methanol (30 ml) was added dropwise over a 45 minute period and a clear solution was obtained. The solvent was removed in vacuo to provide a brown solid residue which was triturated with ether for 64 hours and then filtered. The solid was washed with ether and dried in vacuo at room temperature to provide 2.14 grams of Compound N (89.7% yield) having a melting point of 172° to 174° C.

$^1$H NMR (DMSO-d6): δ 3.02 (multiplet, 2 H, CH$_2$) superimposed over δ 3.07 (singlet, 3 H, 1-CH$_3$); δ 3.65 (singlet, 3 H, ArOCH$_3$); δ 6.80 (singlet, 1 H, ArH).

IR (KBr): 2.85–3.49, 5.83, 6.01, 6.15μ.

Mass spectrum (probe): m/e 293 (M+ of free base).

Anal. Calculated for $C_{14}H_{15}NO_6HBr1.5H_2O$: C, 41.92; H, 4.77; N, 3.49. Found: C, 42.37; H, 4.64; N, 3.51.

EXAMPLE 4

4-β-Carboxyethyl-3-hydroxy-6,7-dimethoxy-1-methylisoquinoline (Compound E)

A slurry of 10.0 grams 4-β-carbomethoxyethyl-3-hydroxy-6,7-dimethoxy-1-methylisoquinoline (32.78 mmol) (Compound B) in 25 ml 1N aqueous hydrochloride acid (25 ml) was stirred at room temperature for 3 days. The precipitate that formed was collected by filtration, was triturated with acetone and ether, and was then dried under vacuum to provide 9.22 grams of the hydrochloride salt of Compound E (86% yield) having a melting point of 117°–119° C. The salt was stirred in 59 ml water at room temperature for 2 hours, and 6.89 grams of Compound E were obtained as a yellow precipitate (72% yield). The precipitate was slurried in hot methanol, filtered hot, washed with ether and dried in vacuo to provide 3.5 grams pure Compound E (36.7%), mp 251°–253° C.

$^1$H NMR (TFA): δ 2.88–3.33 (multiplet, 2 H, CH$_2$CH$_2$COOH); δ 3.33–3.68 (multiplet, 2 H, CH$_2$COOH); δ 4.17 (singlet, 3 H, OCH$_3$); δ 4.23 (singlet, 3 H, OCH$_3$); δ 7.35 (singlet, 1 H, ArH), 7.50 (singlet, 1 H, ArH), 12.57 (broad singlet, 1 H, COOH).

IR (KBr): 2.96–4.67μ.

Mass spectrum (probe): m/e 291 (M+).

Anal. Calculated for $C_{15}H_{17}NO_5$: C, 61.85; H, 5.88; N, 4.87. Found: C, 61.59; H, 6.03; N, 4.83.

EXAMPLE 5

4-β-Carboisopropoxyethyl-3-hydroxy-6,7-dimethoxy-1-methylisoquinoline (Compound R)

4-β-Carboxyethyl-3-hydroxy-6,7-dimethoxy-1-methylisoquinoline (1.00 grams, 3.43 mmol) (Compound E) in 50 ml isopropanol was treated with concentrated sulfuric acid and the mixture was refluxed under a nitrogen atmosphere for 3 hours. The isopropyl alcohol was removed in vacuo. Ice water was added to the oily residue, and the mixture was then extracted with three successive 100 ml portions of methylene chloride. The organic layer was washed with three 100 ml portions of water, two 25 ml portions of a saturated sodium chloride solution, dried over sodium sulfate and the solvent was removed in vacuo to afford 1.10 grams of a yellow solid (96.5% yield) which was pure by thin layer chromatography. Recrystallization from ethyl acetate provided 0.406 grams of pure Compound R (37% yield) having a melting point of 188°–189° C.

$^1$H NMR (CDCl$_3$): δ 1.17 (doublet, J=6 Hz, 6 H, CH(CH$_3$)$_2$); δ 2.40–3.08 (multiplet, 2 H, CH$_2$CH$_2$COOCH(CH$_3$)$_2$); δ 3.27 [triplet, J=7 Hz, 2 H, CH$_2$COOCH(CH$_3$)$_2$]; δ 3.95 (singlet, 3 H, OCH$_3$); δ 4.03 (singlet, 3 H, OCH$_3$); δ 4.98 [multiplet, 1 H, CH(CH$_3$)$_2$); δ 6.85 (singlet, 1 H, ArH); δ 6.95 (singlet, 1 H, ArH).

IR (KBr): 5.78, 6.13, 6.41, 6.71, 6.99μ.

Anal. Calculated for $C_{18}H_{23}NO_5$: C, 64.85; H, 6.95; N, 4.20 Found: C, 64.65; H, 6.86; N, 4.37.

EXAMPLE 6

4-β-Carboxamidoethyl-3-hydroxy-6,7-dimethoxy-1-methylisoquinoline (Compound V)

Ammonium hydroxide (50 ml) was added to a slurry of 2.00 grams of 4-β-carbomethoxyethyl-3-hydroxy-6,7-dimethoxy-1-methylisoquinoline (6.56 mmol) (Compound B) in 50 ml ethanol, and the mixture was stirred at room temperature for 6 days. The yellow precipitate that formed was isolated by filtration, washed with water and then washed with acetone. The solid was dried, and chromatographed on a silica gel column with 15% methanol in chloroform to provide 1.4 grams of pure Compound V (73.7% yield) having a melting point of 259°–261° C.

$^1$H NMR (DMSO-d6): δ 2.62 (singlet, 3 H, 1-CH$_3$); δ 3.80 (singlet, 3 H, OCH$_3$); δ 3.87 (singlet, 3 H, OCH$_3$); δ 7.00 (broad singlet, 2 H, ArH).

IR (KBr): 2.91, 3.13, 5.95, 6.15μ.

Mass spectrum: m/e 290 (M+).

Anal. Calculated for $C_{15}H_{18}N_2O_4$: C, 62.06; H, 6.25; N, 9.65. Found: C, 61.74; H, 6.37; N, 9.57.

By substituting a primary amine or a secondary amine for ammonia in the foregoing procedure, the corresponding secondary or tertiary amides, respectively, were obtained.

EXAMPLE 7a

4-Bromo-3-hydroxy-6,7-dimethoxy-1-methylisoquinoline Hydrobromide Monohydrate (Compound AC)

3-Hydroxy-6,7-dimethoxy-1-methylisoquinoline (1.952 grams, 10 mmol) was dissolved in 80 ml acetic acid by warming the mixture, and the resulting solution was cooled in an ice-water bath with care to avoid solidification of the reaction mixture. To this mechanically stirred mixture, a solution of bromide (0.863 grams or 0.54 ml, 10.5 mmol) in 5 ml acetic acid was added over a 30 minute period. The reaction mixture was periodically scraped with a spatula to dislodge the solid crust from the walls of the reaction flask and was also diluted with additional acetic acid (a total of an additional 100 ml were added in several small portions). The resulting orange-yellow slurry was stirred for an additional 3.5 hours. A yellow solid was isolated by filtration, washed successively with 50 ml acetic acid, 80 ml ethyl acetate and 100 ml diethyl ether, and air-dried to provide 2.99 grams (100%) of Compound AC having a melting point of 175°–178° C.

$^1$H NMR (TFA): δ 3.17 (singlet, 3 H, 1-CH$_3$); δ 4.20 (singlet, 3 H, OCH$_3$); δ 4.27 (singlet, 3 H, OCH$_3$); δ 7.57 (singlet, 1 H, ArH); δ 7.63 (singlet, 1 H, ArH).

IR (KBr): 2.83, 2.94, 3.59, 6.14, 6.67, 7.02μ.

Mass spectrum: m/e 297, 299 (M+).

Anal. Calculated for $C_{12}H_{12}BrNO_3HBrH_2O$: C, 36.29; H, 3.80; N, 3.53; Br, 40.28. Found: C, 35.77; H, 3.56; N, 3.52; Br, 39.45.

EXAMPLE 7b

4-Chloro-3-hydroxy-6,7-dimethoxy-1-methylisoquinoline (Compound AE)

3-Hydroxy-6,7-dimethoxy-1-methylisoquinoline (0.877 grams, 4 mmol) and 0.558 grams N-chlorosuccinimide (4.4 mmol) were stirred and heated to reflux in 80 ml methylene chloride for 16 hours. The slurry was diluted with 50 ml methylene chloride and cooled to room temperature. A yellow solid was isolated by filtration. The solid was washed with methylene chloride, dried and treated with 250 ml chloroform under reflux for 15 minutes. The mixture was filtered hot, and the solid was washed with chloroform to provide 0.72 grams of Compound AE (71.4% yield) having a melting point greater than 300° C. (with decomposition).

$^1$H NMR (TFA): δ 3.13 (singlet, 3 H, 1-CH$_3$); δ 4.20 (singlet, 3 H, OCH$_3$); δ 4.27 (singlet, 3 H, OCH$_3$); δ 7.53 (singlet, 1 H, ArH); δ 7.57 (singlet, 1 H, ArH).

IR (KBr): 6.12, 6.29, 6.71, 7.02, 7.64, 8.03, 8.13μ.

Mass spectrum: m/e 253 (M+).

Anal. Calculated for C$_{12}$H$_{12}$ClNO$_3$: C, 56.82; H, 4.77; N, 5.52; Cl, 13.98 Found: C, 56.39; N, 4.76; N, 5.93; Cl, 13.82.

With N-bromosuccinimide in place of N-chlorosuccinimide and with other substituted 3-hydroxyisoquinoline derivatives as substrates, the foregoing procedure provided the corresponding 4-bromo-3-hydroxyisoquinoline derivatives.

Table 2 lists a number of 2-benzopyrylium salts that were prepared according to the methods described in Examples 8a–8d inclusive and that are useful in the synthesis of the substituted 3-isoquinolinols of this invention.

mixture with diethyl ether 2.246 grams of Compound 8a was separated as a greenish-yellow solid (44% yield) having a melting point of 164°–167° C.

$^1$H NMR (CDCl$_3$): δ 2.62 (triplet, J=7 Hz, 2 H, CH$_2$COOCH$_3$); δ 3.12 (singlet, 3 H, 1-CH$_3$ eclipsing a multiplet of CH$_2$CH$_2$COOCH$_3$); δ 3.55 (singlet, 3 H, COOCH$_3$); δ 4.00 (singlet, 3 H, OCH$_3$); δ 4.13 (singlet, 3 H, OCH$_3$); δ 4.37 (singlet, 3 H, 3-OCH$_3$); δ 6.85 (singlet, 1 H, ArH); δ 6.93 (singlet, 1 H, ArH).

IR (KBr): 5.81, 6.15μ.

EXAMPLE 8b

4-β-Carbomethoxyethyl-3,6,7,8-tetramethoxy-1-methyl-2-benzopyrylium Perchlorate (Compound 8b)

Boron trifluoride etherate (3.0 ml, 24.6 mmol) was slowly added to a solution of 4.0 grams dimethyl 2-(3,4,5-trimethoxyphenyl) glutarate (12.3 mmol) in 4.6 ml acetic anhydride (49 mmol). The solution was heated to 65° C. for 2.5 hours. The mixture was cooled (in an ice bath), and diluted with 180 ml diethyl ether. A 70% perchloric acid solution (17 ml) was added and a yellow precipitate was formed. The mixture was filtered to separate the precipitate which as then washed with diethyl ether and dried to provide 3.53 grams of Compound 8b (64% yield) having a melting point of 117°–119° C.

$^1$H NMR (CDCl$_3$): δ 2.63 (triplet, J=7 Hz, 2 H, CH$_2$CH$_2$COOCH$_3$); δ 3.13 (triplet, J=7 Hz, CH$_2$COOCH$_3$); δ 3.22 (singlet, 3 H, 1-CH$_3$); δ 3.63 (singlet, 3 H, COOCH$_3$); δ 3.93 (singlet, 3 H, OCH$_3$); δ 4.15 (singlet, 6 H, OCH$_3$); δ 4.35 (singlet, 3 H, OCH$_3$); δ 6.95 (singlet, 1 H, Ar—H).

IR (KBr): 3.38, 5.75, 6.15μ.

TABLE 2

2-Benzopyrylium salts

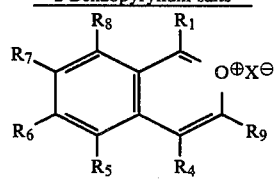

| Prepared According to Example | X$^-$ | R$_1$ | R$_9$ | R$_4$ | R$_5$ | R$_6$ | R$_7$ | R$_8$ | Melting Point °C. |
|---|---|---|---|---|---|---|---|---|---|
| 8b | ClO$_4$ | CH$_3$ | OCH$_3$ | CH$_2$CH$_3$ | H | OCH$_3$ | OCH$_3$ | H | 193–195 |
| 8b | ClO$_4$ | CH$_3$ | OCH$_3$ | CH$_3$ | H | OCH$_3$ | OCH$_3$ | H | 147–149 |
| 8b | ClO$_4$ | CH$_3$ | OCH(CH$_3$)$_2$ | CH$_2$CH(CH$_3$)$_2$ | H | OCH$_3$ | OCH$_3$ | H | 144–146 |
| 8b | ClO$_4$ | CH$_3$ | OCH$_3$ | CH$_2$CH$_3$ | H | OCH$_3$ | OC$_2$H$_5$ | H | |
| 8b | ClO$_4$ | CH$_3$ | OCH$_3$ | c-C$_5$H$_9$ | H | OCH$_3$ | OCH$_3$ | H | |
| 8c | ClO$_4$ | CH$_3$ | OCH$_3$ | CO$_2$CH$_3$ | H | OCH$_3$ | OCH$_3$ | H | |
| 8d | ClO$_4$ | CH$_3$ | NHCOCH$_3$ | H | OCH$_3$ | H | H | H | 167–168 |
| 8d | ClO$_4$ | CH$_3$ | NHCOCH$_3$ | H | OCH$_3$ | OCH$_3$ | H | H | |
| 8d | ClO$_4$ | CH$_3$ | NHCOCH$_3$ | H | H | OCH$_3$ | H | OCH$_3$ | 180–181 |
| 8d | ClO$_4$ | CH$_3$ | NHCOCH$_3$ | H | H | OCH$_3$ | O—n-C$_4$H$_9$ | H | 190–191 |
| 8d | ClO$_4$ | CH$_3$ | NHCOCH$_3$ | H | H | OCH$_3$ | OC$_2$H$_5$ | H | 188–189 |
| 8d | ClO$_4$ | CH$_3$ | NHCOCH$_3$ | H | H | OC$_2$H$_5$ | OC$_2$H$_5$ | H | 158–160 |
| 8d | ClO$_4$ | CH$_3$ | NHCOCH$_3$ | H | H | OC$_2$H$_5$ | CH$_3$ | H | 188–189 |

EXAMPLE 8a

4-β-Carbomethoxyethyl-3,6,7-trimethoxy-1-methyl-2-benzopyrylium Boron Trifluoride salt (Compound 8a)

Boron trifluoride etherate (2.16 ml, 17.68 mmol) was slowly added to a stirred, cooled (in an ice bath) solution of 4.0 grams dimethyl 2-(3,4-dimethoxyphenyl) glutarate (13.49 mmol) in 6.43 ml acetic anhydride (67.49 mmol), and the mixture was stirred at room temperature for 48 hours. Upon dilution and stirring of the

EXAMPLE 8c

3,6,7,8-Tetramethoxy-1-methyl-2-benzopyrylium Perchlorate (Compound 8c)

To a stirred and cooled (ice-bath) solution of 24.8 grams methyl 3,4,5-trimethoxyphenyl-acetate (0.103 mol) in 51.8 grams acetic anhydride (0.508 mol) was slowly added 70% perchloric acid (14 ml, 0.163 mol) over a 20 minute period. The cooling bath was removed, and the mixture was stirred at room temperature for 2 hours. The reaction mixture was cooled again in an ice-bath and 600 ml diethyl ether was added with stirring. The orange crystalline perchlorate salt that precipitated was isolated by filtration, washed with diethyl ether and dried to provide 25.3 grams of Compound 8c (67.2% yield) having a melting point of 160°-162° C. (with decomposition).

$^1$H NMR (CDCl$_3$): δ 3.22 (singlet, 3 H, 1-CH$_3$); δ 3.90 (singlet, 3 H, OCH$_3$); δ 4.23 (singlet, 9 H, OCH$_3 \times 3$); δ 7.42 (singlet, 1 H, ArH); δ 7.45 (singlet, 1 H, ArH).

IR (KBr): 6.08, 6.23, 6.55, 6.78μ.

EXAMPLE 8d

3-Acetamido-7-ethoxy-6-methoxy-1-methyl-2-benzopyrylium Perchlorate (Compound 8d)

To an ice-cooled and stirred solution of 25 grams 4-ethoxy-3-methoxyphenylacetonitrile (0.13 mmol) in 74 ml acetic anhydride (0.785 mol) was slowly added perchloric acid (70%, 11.7 N, 15.5 ml, 0.182 mol) over a 15 minute period. The dark reaction mixture slowly became a yellow slurry and was stirred at room temperature for 42 hours. The mixture was diluted with 200 ml diethyl ether and a crystalline yellow solid was isolated by filtration, washed with diethyl ether and dried in vacuo to provide 47.3 grams of Compound 8d (100% yield) having a melting point of 188°-189° C. (with decomposition).

$^1$H NMR (TFA): δ 1.62 (triplet, J=7 Hz, 3 H, OCH$_2$CH$_3$); δ 2.53 (singlet, 3 H, 3NHCOCH$_3$); δ 3.22 (singlet, 3 H, 1-CH$_3$); δ 4.28 (singlet, 3 H, OCH$_3$); δ 4.42 (q, J=7 Hz, 2 H, OCH$_2$CH$_3$); δ 7.40 (singlet, 1 H, ArH); δ 7.48 (singlet, 1 H, ArH); δ 8.37 (singlet, 1 H, ArH).

IR (KBr): 5.88, 6.10, 6.23, 6.67μ.

Anal. Calculated for C$_{14}$H$_{18}$ClNO$_6$: C, 46.22; H, 4.99; N, 3.85; Cl, 9.75. Found: C, 46.42; H, 4.74; N, 3.82; Cl, 9.65.

EXAMPLE 8e (1)

Dimethyl 2-(2-formyl-4,5-dimethoxyphenyl) glutarate (Compound 8e (1))

To a cold (ice-bath) solution of 10 grams dimethyl 2-(4,5-dimethoxyphenyl) glutarate (33.78 mmol) in 50 ml dry methylene chloride were added 9.0 grams aluminum chloride (67.57 mmol). Dichloromethyl methyl ether (7.77 grams, 67.57 mmol) was added dropwise to the cold solution over a 5 minute period. After the addition was complete, the mixture was stirred for 15 minutes in an ice bath, for 2 hours at room temperature and for an additional 30 minutes in the ice bath. The reaction mixture was poured over 50 ml concentrated hydrochloric acid and ice. The mixture was extracted with four successive 100 ml portions of methylene chloride, and the organic layer was washed with four successive 100 ml portions of water and two successive 100 ml portions of saturated sodium chloride solution and was dried over sodium sulfate. The methylene chloride was evaporated in vacuo to provide 11.48 grams of Compound 8e (1) as an oil.

$^1$H NMR (CDCl$_3$): δ 2.01–2.50 (multiplet, 4 H, CH$_2$CH$_2$COOCH$_3$); δ 3.62 (singlet, 3 H, COOCH$_3$); δ 3.63 (singlet, 3 H, COOCH$_3$); δ 3.92 (singlet, 6 H, Ar—OCH$_3$); δ 6.85 (singlet, 1 H, Ar—H); δ 7.30 (singlet, 1 H, Ar—H); δ 10.2 (singlet, 1 H, CHO).

IR (neat): 5.78, 5.95, 6.25, 6.37, 6.62μ.

Mass spectrum: m/e 324 (M+).

EXAMPLE 8e (2)

Dimethyl 2-(2-formyl-4,5-methylenedioxyphenyl)-glutarate (Compound 8e (2))

To a cooled (ice bath) solution of 1.75 grams methyl 4,5-methylenedioxyphenylacetate (6.24 mmol) in 25 ml dry methylene chloride were added 0.832 grams aluminum chloride (6.24 mmol). Dichloromethyl methyl ether (1.44 grams, 12.47 mmol) was added dropwise to the cold solution over a five minute period. After the addition was complete, the mixture was stirred for 1 hour in an ice bath and for 4 hours at room temperature. The reaction mixture was quenched by pouring over 20 ml concentrated hydrochloric acid and ice, and the resulting solution was extracted with four successive 100 ml portions of methylene chloride. The organic layer was washed with five successive 100 ml portions of water and two successive 50 ml portions of a saturated sodium chloride solution, and dried over sodium sulfate. The methylene chloride was evaporated in vacuo to provide 2.11 grams of Compound 8e (2) as an oily residue.

$^1$H NMR (CDCl$_3$): δ 2.10–2.46 (multiplet, 4 H, CH$_2$CH$_2$COOCH$_3$); δ 2.8 (singlet, 3 H, COOCH$_3$); δ 5.98 (singlet, 2 H, OCH$_2$O); δ 6.82 (singlet, 1 H, ArH); δ 7.20 (singlet, 1 H, Ar—H); δ 10.13 (singlet, 1 H, CHO).

IR (neat): 3.67, 5.76, 5.92, 6.21, 6.73, 6.94μ.

Mass spectrum: m/e 308 (M+).

EXAMPLE 8f

Dimethyl (2-acetyl-4,5-dimethoxyphenyl)malonate (Compound 8f)

To a cold (ice bath) solution of 1.5 grams dimethyl (3,4-dimethoxyphenyl)malonate (5.60 mmol) and 0.88 grams acetyl chloride (11.19 mmol) in dry methylene chloride were added 1.12 grams aluminum chloride (8.4 mmol). After the addition was complete, the mixture was refluxed for 5 hours. The reaction mixture was cooled to room temperature and quenched by pouring onto a mixture of 10 ml concentrated hydrochloric acid and ice. The mixture was extracted with three successive 100 ml portions of methylene chloride, and the organic layer was washed with three successive 100 ml portions of water and two successive 50 ml portions of a saturated sodium chloride solution and was dried over sodium sulfate. The methylene chloride was evaporated in vacuo to provide 2.3 grams of a beige oil which was chromatographed on a column of silica gel. Elution with a 1:3 ethyl acetate/hexane mixture provided 0.73 grams of Compound 8f (42.0% yield) having a melting point of 98°-100° C.

$^1$H NMR (CDCl$_3$): δ 2.57 (singlet, 3H, ArCOCH$_3$) δ 3.75 (singlet, 6H, ArCH(COOCH$_3$)$_2$; δ 3.92 (singlet, 6H, Ar—OCH$_3$); δ 5.67 (singlet, 1H, ArCH): δ 6.92 (singlet, 1H, ArH); δ 7.27 (singlet, 1H, Ar—H).

IR (KBr): 5.68, 5.78, 5.97, 6.21.

Mass spectrum: m/e 310 (M+)μ. Anal. Calculated for C$_{15}$H$_{18}$O$_7$: C, 58.08; H, 5.85. Found: C, 58.33, H, 6.02.

EXAMPLE 8g

Methyl 2-acetyl-4-methoxyphenylacetate (Compound 8g)

To a solution of 11.0 grams 6-methoxy-1-methyl-1-indene in 100 ml acetone at 0° C. was added a solution of 7.0 grams of chromium trioxide in 7.0 ml concentrated sulfuric acid and 50 ml water. The reaction mixture was stirred at 0° C. for two hours before 100 ml water and 100 ml diethyl ether were added. The organic layer was separated and the solvents were removed in vacuo to provide an oily residue. The residue was redissolved in diethyl ether, washed several times with a saturated sodium bicarbonate solution and a saturated sodium chloride solution, and was dried over sodium sulfate. The mixture was evaporated to dryness in vacuo to provide 2.7 grams 2-acetyl-4-methoxyphenylacetic acid ($C_{11}H_{12}O_4$) as yellow crystals (16% yield) having a melting point of 115°–116° C.

$^1$H NMR (CDCl$_3$): δ 2.53 (singlet, 3H, COCH$_3$), δ 3.66 (singlet, 2H, CH$_2$COOCH$_3$); δ 3.92 (singlet, 3H, OCH$_3$); δ 7.00–7.30 (multiplet, 3H, Ar—H).

Mass spectrum: m/e 208 (M+), 193 (BP), 177.

The acid was esterified with methanol in the presence of concentrated sulfuric acid as a catalyst to provide the methyl ester (Compound 8g) as a yellow waxy (low melting) solid.

$^1$H NMR (CDCl$_3$): δ 2.61 (singlet, 3H, COCH$_3$); δ 3.70 (singlet, 3H, COOCH$_3$); δ 3.92 (singlet, 3H, ArOCH$_3$); δ 7.00–7.30 (multiplet, 3H, Ar—H).

Mass spectrum: m/e 222 (M+), 190, 162 (BP)

EXAMPLE 9a(1)

N-(2,3-Dimethoxy-α-phenethyl)diethoxyacetamide (Compound 9a(1))

Thionyl chloride (8.17 grams, 68.6 mmol) was added dropwise to a chilled (ice bath) slurry of 12.73 grams sodium diethoxyacetate (74.9 mmol) in 70 ml diethyl ether. The mixture was refluxed for 3 hours, cooled and transferred to an addition funnel. This solution was added dropwise to a chilled (ice bath) solution of 11.28 grams 2,3-dimethoxy-α-phenethylamine (62.4 mmol) in 30 ml benzene and 20 ml pyridine. The mixture was refluxed under nitrogen for one hour, allowed to cool to room temperature, and poured into 100 ml ice water. The organic phase was separated and the aqueous phase was extracted with three 200 ml portions of diethyl ether. The combined organic phases were washed with two 100 ml portions of 0.5N hydrochloric acid and a saturated aqueous sodium chloride solution, and filtered through phase-separating filter paper. The solvent was evaporated in vacuo to provide 6.8 grams of crude Compound 9a(1) (35% yield). The product was chromatographed on silica gel CC7 (250 grams, 45 mm ID column) and was eluted with a 20:80 ethyl acetate:hexane mixture to provide 5.22 grams of pure Compound 9a(1) (26.9% yield).

$^1$H NMR (CDCl$_3$): δ 1.20 (triplet, J=7 Hz, 3H, OCH$_2$CH$_3$); δ 1.27 (triplet, J=7 Hz, 3H, OCH$_2$CH$_3$); δ 1.47 (doublet, J=7 Hz, 3H, CH—CH$_3$); δ 3.60 (quartet, J=7 Hz, 2H, OCH$_2$CH$_3$); δ 3.67 (quartet, J=7 Hz, 2H, OCH$_2$CH$_3$); δ 3.85 (singlet, 3H, ArOCH$_3$); δ 3.93 (singlet, 3H, Ar—OCH$_3$); δ 4.75 (singlet, 1H, CHOC$_2$H$_5$); δ 5.22 (triplet, J=7 Hz, 1H, CHCH$_3$); δ 6.85 (multiplet, 3H, Ar—H); δ 7.33 (broad singlet, 1H, N—H).

IR (neat): 2.92, 3.36, 5.95, 6.33, 6.76μ.

Mass spectral peaks: m/e 311 (M+).

Anal. Calculated for $C_{16}H_{25}NO_5$: C, 61.72; H, 8.09; N, 4.50. Found: C, 61.55; H, 8.01; N, 4.69.

EXAMPLE 9a(2)

N-(2,3-Dimethoxybenzyl)diethoxyacetamide (Compound 9a(2))

Substitution of 2,3-dimethoxybenzylamine for 2,3-dimethoxy-α-phenethylamine in the foregoing Example provided Compound 9a(2) in 33% yield.

$^1$H NMR (CDCl$_3$): δ 1.23 (triplet, J=7 Hz, 6H, 2×CH$_2$CH$_3$); δ 3.63 (quartet, J=7 Hz, 4H, 2×CH$_2$CH$_3$); δ 3.87 (singlet, 6H, Ar—OCH$_3$); δ 6.88 (multiplet, 3H, Ar—H).

IR (neat): 2.99, 3.36, 5.95, 6.33, 6.76μ.

Mass spectrum: m/e 297 (M+).

Anal. Calculated for $C_{15}H_{23}NO_5$: C, 60.59; H, 7.80; N, 4.71. Found: C, 60.19; H, 7.88; N, 4.66.

EXAMPLE 9b

N-(2,3-Dimethoxybenzyl)diethoxyacetamide (Compound 9b)

2,3-Dimethoxybenzyl chloride (1 equivalent) was added to a slurry of sodium hydride (1.05 equivalents), diethoxyacetamide (1.05 equivalents) and sodium iodide (1 equivalent) in tetrahydrofuran, and the mixture was heated to reflux for 24 hours. Compound 9b having the same spectral and physical characteristics as described under Example 9a(2), was obtained after workup and purification.

Table 3 lists a number of phenylacetates and phenylacetonitriles that were prepared according to the methods described in Examples 10a–10c inclusive and that are useful in the synthesis of the substituted 3-isoquinolinols of this invention.

TABLE 3

Phenylacetates (II, A = CO$_2$R) or Phenylacetonitriles (II, A = CN)

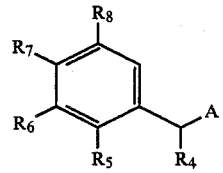

| Prepared According to Example | A | R$_4$ | R$_5$ | R$_6$ | R$_7$ | R$_8$ |
|---|---|---|---|---|---|---|
| 10b | CO$_2$CH$_3$ | (CH$_2$)$_2$CO$_2$CH$_3$ | H | OCH$_3$ | OCH$_3$ | H |
| 10b | CO$_2$CH$_3$ | (CH$_2$)$_2$CO$_2$CH$_3$ | H | OCH$_3$ | OCH$_3$ | OCH$_3$ |
| 10b | CO$_2$CH$_3$ | (CH$_2$)$_2$CO$_2$CH$_3$ | H | O—CH$_2$—O | | H |
| 10b | CO$_2$CH$_3$ | CH$_2$CH(CH$_3$)CO$_2$CH$_3$ | H | OCH$_3$ | OCH$_3$ | H |
| 10b | CN | (CH$_2$)$_2$CO$_2$CH$_3$ | H | O—CH$_2$—O | | H |
| 10a | CO$_2$CH$_3$ | CH$_2$CH$_3$ | H | OCH$_3$ | OCH$_3$ | H |
| 10a | CO$_2$CH$_3$ | (CH$_2$)$_2$CH$_3$ | H | OCH$_3$ | OCH$_3$ | H |
| 10a | CO$_2$CH(CH$_3$)$_2$ | CH(CH$_3$)$_2$ | H | OCH$_3$ | OCH$_3$ | H |
| 10a | CO$_2$CH$_3$ | c-C$_5$H$_9$ | H | OCH$_3$ | OCH$_3$ | H |

TABLE 3-continued

Phenylacetates (II, A = CO$_2$R) or Phenylacetonitriles (II, A = CN)

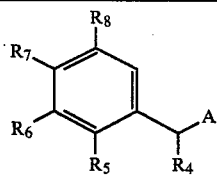

| Prepared According to Example | A | R$_4$ | R$_5$ | R$_6$ | R$_7$ | R$_8$ |
|---|---|---|---|---|---|---|
| 10a | CO$_2$CH$_3$ | CH$_3$ | H | OCH$_3$ | OCH$_3$ | H |
| 10a | CO$_2$CH$_3$ | CH$_2$CH$_3$ | H | OCH$_3$ | OC$_2$H$_5$ | H |
| 10c | CN | H | H | OCH$_3$ | O—n-C$_4$H$_9$ | H |
| 10b | CO$_2$CH$_3$ | [(CH$_2$)$_2$CO$_2$CH$_3$]$_2$ | H | OCH$_3$ | OCH$_3$ | H |

EXAMPLE 10a

Dimethyl 2-(3,4-Dimethoxyphenyl)butyrate (Compound 10a)

To a slurry of 0.857 grams sodium hydride (35.71 mmol from 1.74 grams of a 50% oil-dispersion washed with hexanes) in 100 ml N,N-dimethylformamide were added 10 grams 3,4-dimethoxyphenylacetate (47.62 mmol) in 25 ml N,N-dimethylformamide dropwise over a 5 minute period. The mixture was stirred at room temperature for 2 hours, cooled by an ice bath, and 10.64 grams iodoethane (69.92 mmol) were added. The mixture was diluted with 500 ml cold water after 1 hour, extracted with four successive 100 ml portions of methylene chloride, washed with four successive 100 ml portions of water and two successive 25 ml portions of a saturated sodium chloride solution, and was dried over sodium sulfate. The methylene chloride was evaporated in vacuo to provide 7.10 grams of a dark residue which was chromatographed on a column of silica gel. Elution with a 10:90 ethyl acetate:hexane mixture provided 3.34 grams of Compound 10a as a colorless liquid after evaporation of the solvent and drying under vacuum (59% yield).

$^1$H NMR (CDCl$_3$): δ 0.88 (triplet, J=7 Hz, 3H, CH$_2$CH$_3$); δ 1.53–2.17 (multiplet, 2H, CH$_2$CH$_3$); δ 3.37 (triplet, J=7 Hz, 1H, ArCH); δ 3.63 (singlet, 3H, CO$_2$CH$_3$); δ 3.82 (singlet, 3H, OCH$_3$); δ 3.85 (singlet, 3H, OCH$_3$); δ 6.78 (singlet, 3H, Ar—H).

IR (KBr): 5.76, 6.29, 6.60μ.

Mass spectrum: m/e 238 (M+).

Anal. Calculated For C$_{13}$H$_{18}$O$_4$: C, 65.53; H, 7.61. Found: C, 65.64; H, 7.70.

EXAMPLE 10b

Dimethyl 2-(3,4,5-trimethoxyphenyl)glutarate (Compound 10b)

Methyl acrylate (15.5 grams, 17.9 mmol) was added to a solution of 3.92 grams of methylphenylacetate (16.3 mmol) and 0.8 grams sodium methoxide (14.8 mmol) in 350 ml acetonitrile. The reaction mixture was stirred at room temperature for 16 hours and was then quenched by adding 10 ml acetic acid. The solvent was removed in vacuo to provide 60 grams of crude Compound 10b. A portion of the crude material (20.1 grams) was chromatographed on silica gel AR CC7 (600 grams, 75 mm ID column) and eluted with a 3:1 ethyl acetate:hexane mixture to provide 12.7 grams of pure compound 10b (74% yield) as a colorless crystalline solid having a melting point of 46°–48° C.

$^1$H NMR (CDCl$_3$): δ 2.28 (multiplet, 4H, CH$_2$CH$_2$COOCH$_3$); δ 3.33 (multiplet, 1H, CH—CH$_2$); δ 3.65 (singlet, 3H, COOCH$_3$); δ 3.68 (singlet, 3H, COOCH$_3$); δ 3.82 (singlet, 3H, 4—OCH$_3$); δ 3.83 (singlet, 6H, 3,5-OCH$_3$); δ 6.48 (singlet, 2H, Ar—H).

IR (KBr): 3.37, 5.76, 6.29, and 6.62μ.

Mass spectrum: m/e 326 (M+).

Anal. Calculated for C$_{16}$H$_{22}$O$_7$: C, 58.89; H, 6.79. Found: C, 58.90; H, 6.90.

EXAMPLE 10c 4-n-Butoxy-3-methoxyphenylacetonitrile (Compound 10c)

A mixture of 15 grams 4-hydroxy-3-methoxyphenylacetonitrile (91.91 mmol), 26.40 ml (33.59 grams) n-butyl bromide (245 mmol) and 21.17 grams potassium carbonate (153.2 mmol) in 150 ml acetone was heated to reflux under nitrogen for 18 hours. After cooling to room temperature, the mixture was diluted with diethyl ether and the inorganic salts were removed by filtration and were washed with diethyl ether. The filtrate and wash solutions were evaporated in vacuo to provide 21.11 grams of Compound 10c as a straw-colored viscous oil (99.9% yield) which was dried in vacuo at 50° C.

$^1$H NMR (CDCl$_3$): δ 0.97 (triplet, J=7 Hz, 3H, 4—CH$_3$(CH$_2$)$_3$—O); δ 1.20–2.10 (multiplet, 4H, CH$_3$(CH$_2$)$_2$—CH$_2$O); δ 3.67 (singlet, 2H, CH$_2$CN); δ 3.87 (singlet, 3H, 3—CH$_3$O); δ 4.0 (triplet, J=7 Hz, 2H, CH$_2$O); δ 6.82 (singlet, 3H, Ar—H).

IR (neat): 4.44, 6.29, 6.62, 7.93μ.

Mass spectrum: m/e 219 (M+).

Anal. Calculated for C$_{13}$H$_{17}$NO$_2$: C, 71.21; H, 7.81; N, 6.39. Found: C, 70.89; H, 7.81; N, 6.28.

RESULTS

A. Cardiotonic Activity

The acute in vivo cardiotonic activity of compounds prepared according to the present invention was determined according to a modification of the procedure described by Alousi et al., Circ. Res., 45, 666 (1979).

In particular, adult mongrel dogs were anesthetized with sodium pentobarbital and were artificially respired. Arterial pressure was monitored via a femoral artery, and the pulse pressure was used to trigger a cardiotachometer for heart rate. Left ventricular pressure was determined with a Millar catheter, and dP/dt (the change in ventricular pressure with time) was derived. Cardiac output was determined by measuring ascending aortic blood flow with an electromagnetic flow probe, and myocardial contractile force was measured with a Walton Brodie strain gauge sutured to the right ventricle. Lead II EKG was also recorded.

A standard dose (10 μg/kg/min) of dopamine was administered to assess myocardial responsiveness.

Compounds of the invention were administered by intravenous infusion or bolus oral administration, and the effects on cardiovascular parameters were determined. The total amount of each compound that was administered is shown in Table 4, hereinafter.

Dose related effects of the test compound on blood pressure (BP), heart rate (HR), maximum change in left ventricular pressure with time (dP/dt max),% change in cardiac force (CF) and the increase in mean arterial blood pressure relative to controls (MABP) were compared to pretreatment control values, expressed as a% change and rated for activity. Data for the isoquinolinols of this invention are summarized in Table 4.

B. Renal Vasodilating Activity

Goldberg et al, *J. Pharmacol. Exp. Ther.*, 163, 188 (1968), performed an investigation of the structural requirements for dopamine-like renal vasodilation of phenethylamines and apomorphine. The following procedure is a variation of the assay described in that report.

Adult mongrel dogs were anesthetized and surgically prepared for electromagnetic measurement of renal artery blood flow. A carotid artery was cannulated for measuring arterial blood pressure, and drugs were administered intravenously. Heart rate was monitored with a cardiotachometer. Renal vascular resistance was calculated as the ratio of mean arterial blood pressure/renal artery blood flow. Dopamine was infused intravenously at 3 μg/kg/min for ten minutes (at an infusion rate of about 1 ml/min) to determine responsiveness of each dog to renal dopamine receptor stimulation. Cumulative dose-response data were obtained by infusing a compound of this invention at progressively increasing (usually three-fold) infusion rates, each dose being infused for five minutes. The maximum % increase from pre-drug control in renal artery blood flow (or a decrease in renal vascular resistance) was determined for each infusion dose.

Data for the isoquinolinols of this invention are summarized in Table 4. RBF values are percent change in renal blood flow. RVR values are percent change in renal vascular resistance. MABP and HR are percent changes in mean arterial blood pressure and heart rate, respectively, relative to controls.

TABLE 4

Representative Cardiotonic and Renal Vasodilator Activities of Isoquinolinols

| COMPOUND | CARDIOTONIC | | | | | RENAL VASODILATOR | | | | |
|---|---|---|---|---|---|---|---|---|---|---|
| | DOSE* | CF | dP/dt | HR | MABP | DOSE* | RBF | RVR | MABP | HR |
| A | N.T. | | | | | 13.9 | +30 | −30 | −9 | +14 |
| B | 0.875 | 140 | 78 | 34 | −12 | 13.9 | +15 | −38 | −28 | +12 |
| C | 0.875 | 62 | 51 | 10 | −6 | N.T. | | | | |
| D | 8.75 | 60 | 34 | 13 | −7 | 13.9 | +21 | −27 | −11 | +3 |
| E | 1.875 | 75 | 42 | 5 | −3 | 13.9 | +7 | −13 | −7 | +11 |
| G | 3.75 | 82 | 32 | 13 | −10 | 13.9 | +11 | −14 | −5 | −3 |
| H | 0.875 | 76 | 45 | 13 | −2 | 13.9 | +41 | −38 | −12 | +20 |
| I | N.T. | | | | | 13.9 | +35 | −29 | −4 | +38 |
| J | 0.875 | 22 | 20 | 8 | −4 | 13.9 | +18 | −23 | −13 | −2 |
| K | 0.875 | 47 | 33 | 10 | −3 | 13.9 | +28 | −28 | −8 | +7 |
| L | 0.875 | 131 | 118 | 38 | −21 | N.T. | | | | |
| M | 1.875 | 17 | 19 | 2 | −4 | | | | | |
| O | 1.875 | 100 | 67 | 21 | 0 | 13.9 | +15 | −18 | −15 | −9 |
| P | 1.875 | 15 | 17 | 7 | 3 | | | | | |
| Q | 0.875 | 53 | 24 | 7 | −4 | 13.9 | +42 | −23 | −7 | +10 |
| R | 1.875 | 22 | 15 | 3 | −6 | N.T. | | | | |
| S | 0.875 | 60 | 20 | 8 | −4 | N.T. | | | | |
| T | 0.875 | 23 | 29 | 9 | −3 | N.T. | | | | |
| U | 1.875 | 26 | 28 | 6 | 0 | N.T. | | | | |
| W | 0.875 | 42 | 28 | 6 | −1 | 13.9 | +64 | −62 | −38 | −6 |
| X | 0.875 | 40 | 24 | 4 | −5 | N.T. | | | | |
| Y | 0.375 | 84 | 44 | 12 | −16 | 13.9 | +10 | −13 | −4 | +8 |
| Z | 0.025 | 143 | 98 | 13 | −12 | 1.2 | +10 | −38 | −32 | +30 |
| AB | 0.100 | 80 | 48 | 15 | −4 | | | | | |
| AC | 0.875 | 128 | 25 | 26 | −40 | 0.2 | +8 | −27 | −21 | +46 |
| AD | 1.875 | 111 | 106 | 21 | −3 | 5.0 | +16 | −32 | −20 | +15 |
| AE | 0.875 | 89 | 88 | 29 | 1 | 0.14 | +12 | −25 | −16 | +68 |
| AF | 0.150 | 92 | 60 | 8 | −15 | 0.2 | +11 | −24 | −16 | +28 |
| AG | 1.875 | 88 | 51 | 28 | −22 | 1.2 | +10 | −34 | −27 | +27 |
| AH | 0.375 | 50 | 46 | 6 | −3 | 1.2 | +13 | −17 | −6 | +25 |
| AI | 0.925 | 65 | 56 | 8 | 0 | 1.2 | +7 | −7 | −1 | +4 |
| AJ | 1.875 | 39 | 25 | 10 | −6 | 6.2 | +9 | −4 | +4 | +2 |
| AK | 0.375 | 114 | 39 | 13 | −5 | 0.2 | +10 | −11 | −2 | +10 |
| AL | 0.375 | 138 | 46 | 22 | −10 | 1.2 | +13 | −17 | −6 | +9 |
| AN | 1.875 | 46 | 22 | 5 | 3 | 0.34 | +10 | −10 | −1 | +1 |
| AQ | N.T. | | | | | 1.2 | +13 | −12 | 0 | +16 |
| AS | 0.125 | 78 | 49 | 8 | −10 | 6.2 | +9 | −11 | −1 | +2 |
| AU | N.T. | | | | | 6.2 | +20 | −10 | 0 | −3 |
| AV | 1.87 | 89 | 34 | 14 | −2 | 1.2 | +22 | −13 | +5 | +1 |

TABLE 4-continued

Representative Cardiotonic and Renal Vasodilator Activities of Isoquinolinols

| COMPOUND | CARDIOTONIC | | | | | RENAL VASODILATOR | | | | |
|---|---|---|---|---|---|---|---|---|---|---|
| | DOSE* | CF | dP/dt | HR | MABP | DOSE* | RBF | RVR | MABP | HR |
| AW | N.T. | | | | | 6.2 | +20 | −34 | −17 | +59 |

*Dose: Intravenous, milligrams of compound per kilogram body weight.
N.T. indicates "not tested".
CF is cardiac force.
dP/dt is the maximum change left ventricular pressure with time.
HR is the percent change in heart rate.
MABP is the mean arterial blood pressure.
RBF is the renal blood flow.
RVR is the renal vascular resistance.
All values are expressed as percent change relative to controls.

As shown in Table 4, the preferred compounds of this invention produce an increase in cardiac force, an increase in the left ventricular dP/dt and minor changes in heart rate and mean arterial blood pressure. Examples of preferred compounds for use and cardiotonics include Compounds B, L, Y, Z, AD, AF, AG, AK and AL.

The preferred compounds of this invention also produce an increase in renal blood flow, a decrease in renal vascular resistance, with minor changes in mean arterial blood pressure and heart rate. Examples of preferred compounds for use as vasodilators include Compounds A, B, D, H, K, Q, W, Y, Z, AD, AF, AG, AH, AK, AL, AN, AQ and AV.

C. Inhibition of Phosphodiesterase fraction III Activity

Thompson et al. described a cyclic nucleotide phosphodiesterase assay in *Advances in Cyclic Nucleotide Research*, Brooker et al., eds., 10, 69–92 (1979). The following produce is based on that published assay and measures the ability of compounds to inhibit cyclic nucleotide phosphodiesterase which is an enzyme that converts either cyclic AMP or cyclic GMP to the non-cyclized AMP or GMP, respectively.

Compounds were tested at various concentrations in the presence of cyclic AMP (0.10–1.0 uM containing 0.2 microCuries $^3$H-cyclic AMP), cyclic nucleotide phosphodiesterase, and 0.05M Tris-Cl buffer (pH 7.4, containing 5 mM magnesium chloride). After a specified time, the reaction was stopped by heating to 100° C. for 1 minute. After cooling, 0.10 ml of a solution containing snake venom (1 mg/ml) was added, and the reaction was allowed to proceed for 30 min. Termination of this reaction was accomplished by the addition of 1.0 ml of 33 percent DOWEX AG1×8 resin slurry (Dow Chemical Co., Midland, MI) to separate the product from the unconverted substrate. An aliquot was removed from the supernatant and analyzed by liquid scintillation spectrometry.

The fraction III enzyme was isolated as an isozyme from the crude canine heart homogenate by ion exchange chromatography. The enzyme activity was designated fraction III since it is the third and last phosphodiesterase activity to be eluted from the chromatographic column. The fraction III enzyme has a relatively high affinity and specificity for the cyclic AMP.

Data are presented as the IC$_{50}$ which is the concentration (in micromoles) of a compound that was required to inhibit 50 percent of the cyclic nucleotide phosphodiesterase activity.

Data for the isoquinolinols of this invention are summarized in Table 5.

TABLE 5

Inhibition of Phosphodiesterase Activity by Isoquinolinols

| Compound | Phosphodiesterase fraction III Inhibition (IC$_{50}$ in uM) |
|---|---|
| B | 40.0 |
| Y | 5.0 |
| Z | 2.4 |
| AB | 8.3 |
| AC | 10.0 |
| AD | 11.0 |
| AE | 62.0 |
| AF | 12.3 |
| AH | 80 |
| AI | 160 |
| AL | 37 |
| AN | 128 |

As shown in Table 5, the preferred compounds of this invention that inhibit phosphodiesterase fraction III activity include Compounds B, Y, Z, AB, AC, AD, AF and AL.

As demonstrated by the combination of the foregoing results, the most preferred compounds of this invention include Compounds B, Y, Z, AD, AF and AL which are identified in Table 1 herein. Each of these compounds exhibits a combination of cardiotonic properties, renal vasodilating properties and phosphodiesterase fraction III inhibiting properties. A particularly preferred compound is Compound Z—4-ethyl-3-hydroxy-6,7-dimethoxy-1-methylisoquinoline.

The present invention has been described with reference to several preferred embodiments. It will be understood, however, that numerous modifications and variations of the disclosed subject matter can be made without departing from the scope of the invention described herein.

What is claimed is:

1. A compound having a structure that corresponds to the formula:

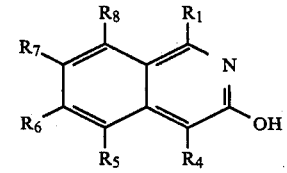

wherein R$_1$ is a radical selected from the group consisting of hydrogen, lower alkyl, phenyl, substituted phenyl wherein the substituent is lower alkyl; halo lower alkyl and halo phenyl;

R$_4$ is a radical selected from the group consisting of hydrogen, halogen, lower alkyl, cycloalkyl, having 5–7 carbon atoms and —(CH$_2$)$_n$—Y wherein Y is, OR, OCOR, CF$_3$, COR, CON(R)$_2$, and halogen, wherein R is hydrogen, lower alkyl and cycloalkyl having 5–7 carbon atoms and n is an integer from 1 to 10, inclusive; and R$_5$–R$_8$ are independently selected from the group consisting of hydrogen, halogen, hydroxy, and lower alkoxy; and the pharmaceutically acceptable salts thereof.

2. The compound according to claim 1 wherein R$_1$ is lower alkyl or halogen-substituted lower alkyl, R$_4$ is selected from the group consisting of hydrogen, halogen, and lower alkyl, R$_5$ is hydrogen, R$_6$ and R$_7$ are each lower alkoxy and R$_8$ is hydrogen or methoxy.

3. The compound according to claim 1 wherein R$_1$ is methyl, R$_4$ is lower alkyl, R$_5$ is hydrogen, R$_6$ and R$_7$ are methoxy or ethoxy and R$_8$ is hydrogen.

4. A compound according to claim 1 which is selected from 4-ethyl-3-hydroxy-6,7-dimethoxy-1-methylisoquinoline and 3-hydroxy-4-isopropyl-6,7-dimethoxy-1-methylisoquinoline.

5. A compound according to claim 1 which is selected from the group consisting of 4-(β-carbomethoxyethyl)-3-hydroxy-6,7-dimethoxy-1-methylquinoline; 4-(β-carbomethoxyethyl)-3-hydroxy-6,7-methylenedioxy-1-methylisoquinoline; 4-(β-carbomethoxymethyl)-3-hydroxy-6,7-dimethoxy-1-methylisoquinoline; and 4-bromo-3-hydroxy-6,7-dimethoxy-1-methylisoquinoline.

6. A pharmaceutical composition comprising an effective amount of a compound according to claim 1 as active ingredient dispersed in a pharmaceutically acceptable carrier.

7. A method for increasing the contractile force of cardiac muscle in a mammal comprising administering to said mammal a unit dose of the pharmaceutical composition according to claim 6.

* * * * *